United States Patent [19]

Robinson et al.

[11] Patent Number: 4,838,269

[45] Date of Patent: Jun. 13, 1989

[54] MANIFOLD FOR ANGIOPLASTY BALLOON CATHETER

[75] Inventors: David B. Robinson, Chanhassen; William H. Penny, St. Anthony, both of Minn.

[73] Assignee: SciMed Life Systems, Inc., Maple Grove, Minn.

[21] Appl. No.: 172,659

[22] Filed: Mar. 24, 1988

[51] Int. Cl.⁴ .............................................. A61M 29/02

[52] U.S. Cl. .................................... 128/344; 128/657; 604/96; 604/165

[58] Field of Search .................................. 604/96–102, 604/283, 165, 167; 128/344, 348.1, 657

[56] References Cited

U.S. PATENT DOCUMENTS

| | | | |
|---|---|---|---|
| 4,195,637 | 4/1980 | Grüntzig et al. | 128/348.1 |
| 4,332,254 | 6/1982 | Lundquist | 128/344 |
| 4,582,181 | 4/1986 | Samson | 128/348.1 |
| 4,641,654 | 2/1987 | Samson et al. | 128/344 |
| 4,646,742 | 3/1987 | Packard et al. | 128/344 |
| 4,655,746 | 4/1987 | Daniels et al. | 604/53 |
| 4,664,113 | 5/1987 | Frisbie et al. | 128/344 |
| 4,730,616 | 3/1988 | Frisbie et al. | 128/348.1 |

FOREIGN PATENT DOCUMENTS

WO86/06285 11/1986 PCT Int'l Appl. .

OTHER PUBLICATIONS

SciMed Life Systems, Inc., "Angioplasty," Publication No. IMPMP 11-86 (1986).

Versaflex Delivery Systems, Inc., "Flexibility, Trackability, Pushability, and Low-Profile Coiled Into One," 1988 brochure distributed by Medtronic (Minneapolis, MN 55432).

C. R. Bard, Inc., Catalog, "PTCA Accessories," showing Disposable PTCA Y-Adapters, catalog No. 006055, p. 13.

*Primary Examiner*—Stephen C. Pellegrino
*Attorney, Agent, or Firm*—Kinney & Lange

[57] ABSTRACT

A manifold for a double lumen angioplasty balloon catheter has a first chamber connecting the balloon lumen to a first port, a second chamber connecting the guide wire lumen to a second port and a guide wire entry port, an adjustable guide wire seal and a mounting system for an alternative elastic diaphragm guide wire feeding device. An override system for the adjustable guide wire seal is also disclosed.

20 Claims, 3 Drawing Sheets

MANIFOLD FOR ANGIOPLASTY BALLOON CATHETER

BACKGROUND OF THE INVENTION

1. Field of the Invention

The present invention relates to a manifold for dilation catheters used in coronary angioplasty.

2. Description of the Prior Art

Percutaneous transluminal coronary angioplasty is a procedure for dilating coronary arteries which are partially occluded or blocked. A special catheter which carries an inflatable dilation balloon at the distal end is employed to reshape a partially occluded artery. The balloon is inserted in a deflated condition in the restricted portion of the artery and inflated by filling with a pressurized radioopaque fluid. In this way, the occluded lumen is reshaped by the dilation balloon to allow better passage of blood. The obstructing material is neither dislocated nor removed from the vessel, but rather pressed against the wall. The wall, in turn, is stretched to accommodate the previously obstructing material. After the lumen has been reshaped, the dilation balloon is deflated and removed. The site of the formed obstruction is examined and, if necessary, the procedure is repeated until the obstructed segment remains open.

The technique is more fully explained in the Gruntzig et al. U.S. Pat. No. 4,195,637. The Gruntzig Patent shows conventional tube connections at the proximal end of a catheter. One connection is to a pressure measuring device with a suction-pressure pump. The same lumen is also connected to a roller pump through a second connector. The Gruntzig method incorporates a guide catheter within a dilating catheter having a double lumen support or carrier tube.

The Sampson U.S. Pat. Nos. 4,582,181 and 4,641,654 disclose low profile dilation catheters and integral guide wires for steering the catheters into an artery system. The steerable balloon dilation catheter assemblies disclosed have dye injection and pressure measurement capabilities associated with the guide wire lumen. At the proximal end of the catheter, a first fitting is coupled to the balloon lumen and a second fitting is in communication with the guide wire lumen. The relative sizes of the guide wire lumen and the guide wire are such that dye injections and/or pressure measurements may be performed through the second fitting. Sampson also discloses a compressive O-ring seal at the proximal end of the second fitting which seals about the guide wire. A guide wire rotation facilitating device is coupled to the guide wire at the proximal end.

The Packard et al. U.S. Pat. No. 4,646,742 discloses an angioplasty catheter having a hub on the proximal end of the catheter body to facilitate the manipulation of a distally located valve and useful for introduction of a perfusant along the length of the catheter body.

The Daniels et al. U.S. Pat. No. 4,655,746 discloses a catheter device for transferring fluid material to or from a selected-length segment of vessel. The device includes a pair of inflatable balloon catheters. The catheter includes a two-armed manifold connected to a flanged end of a tube. A guide wire is lead through an O-ring seal to a wheel mounting for rotating the guide wire. The two-armed manifold in turn leads to a second two-armed manifold which in turn leads to a three-armed manifold.

The Frisbie et al. U.S. Pat. No. 4,664,133 discloses a steerable dilation catheter assembly having an adapter with at least one arm. The proximal end of a guide wire extends through the adapter. A rotation limiting device is secured to the proximal end of the guide wire and an O-ring seal may be tightened by a thumb screw of the rotation limiting device.

WO 86/06285 discloses a balloon angioplasty system with a microdilation probe which can be passed through the main lumen of the dilation catheter.

The above described patents provide compressive seals at the proximal end of the guide wire or guide catheter. An alternative to a compressive seal is an elastic diaphragm. Elastic diaphragms may be punctured by the physician or purchased pre-punctured. For example, United States Catheter Corp. (a division of C.R. Bard, Inc.), Billerica, Mass., sells elastic diaphragm containing Y-type adapters (see Catalog Nos. 006055, 006056 and 006057). To a large extent, the choice of a compressive seal or a diaphragm seal is a matter of personal preference to the physician performing the angioplasty procedure.

One problem with compressive seals is the potential for separation of the compressive nut, also known as a hemostatic valve nut, from the valve unit. Another problem is undesired rotation of the hemostatic valve nut during the angioplasty procedure. Such undesired rotation can result in an alteration of the resistive force of the seal on the guide wire, as the guide wire is pushed into the patient to create the path to the stenosis.

SUMMARY OF THE INVENTION

The invention is a manifold for an angioplasty balloon catheter having a first lumen connected to a balloon and a second lumen for passing a guide wire. The manifold includes a first chamber connecting the first lumen to a first port, a second chamber connecting the second lumen to a second port and a guide wire entry port, a compressive O-ring seal which may be applied to the guide wire at the guide wire entry port and a mounting system for coupling an elastic diaphragm guide wire feed through device to a hemostatic valve nut. Additionally, an optional O-ring between shoulders on the manifold and the hemostatic valve nut allows the hemostatic valve seal to be overridden when employing the elastic diaphragm guide wire feed through device.

DESCRIPTION OF THE PREFERRED EMBODIMENTS

Figure 1:
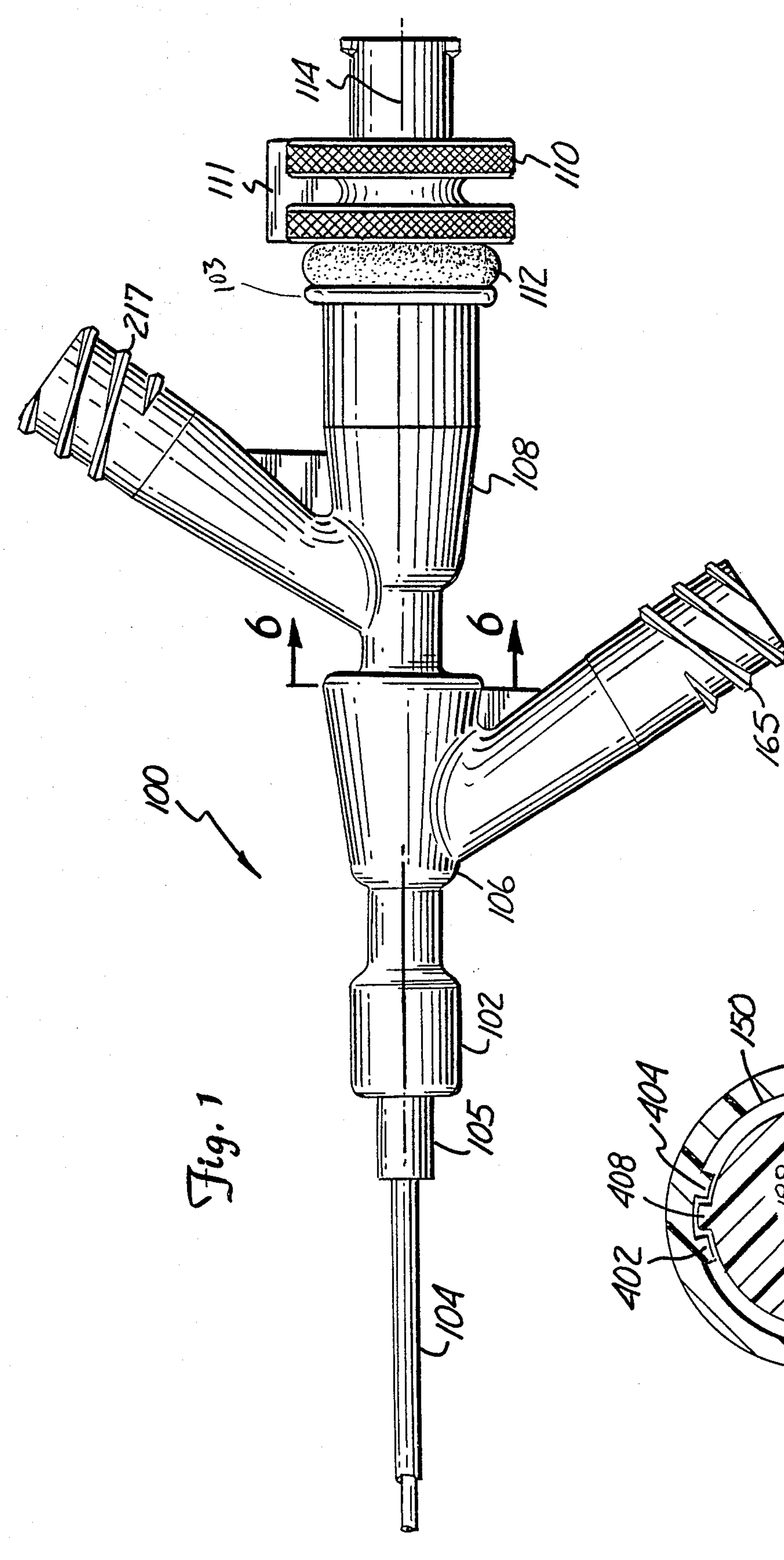
FIG. 1 is a top view of the preferred embodiment.

The manifold of this invention is generally shown at 100 in FIG. 1. The manifold 100 is connected at a distal end 102 to a double lumen catheter 104. A strain relief sleeve 105 protects the catheter 104 from kinking immediately adjacent to the distal end 102 of the manifold 100. The manifold 100 includes a balloon manifold 106 which provides access to an inflatable balloon (not shown) which is distally located on the catheter 104. The manifold 100 also includes a thru/dye manifold 108 which provides access for a guide wire (not shown). The thru/dye manifold has a proximal end 103. The manifold 100 also includes a hemostatic valve nut 110 which is proximally located on the manifold 100.

In one embodiment, the manifold 100 also includes a face-sealing O-ring 112 interposed between the thru/-dye manifold 108 and the hemostatic valve nut 110. The manifold 100 has an axis 114 which is centrally and longitudinally located. When installed, a guide wire (not shown) generally follows the central axis 114 through the manifold 100.

Figure 2:
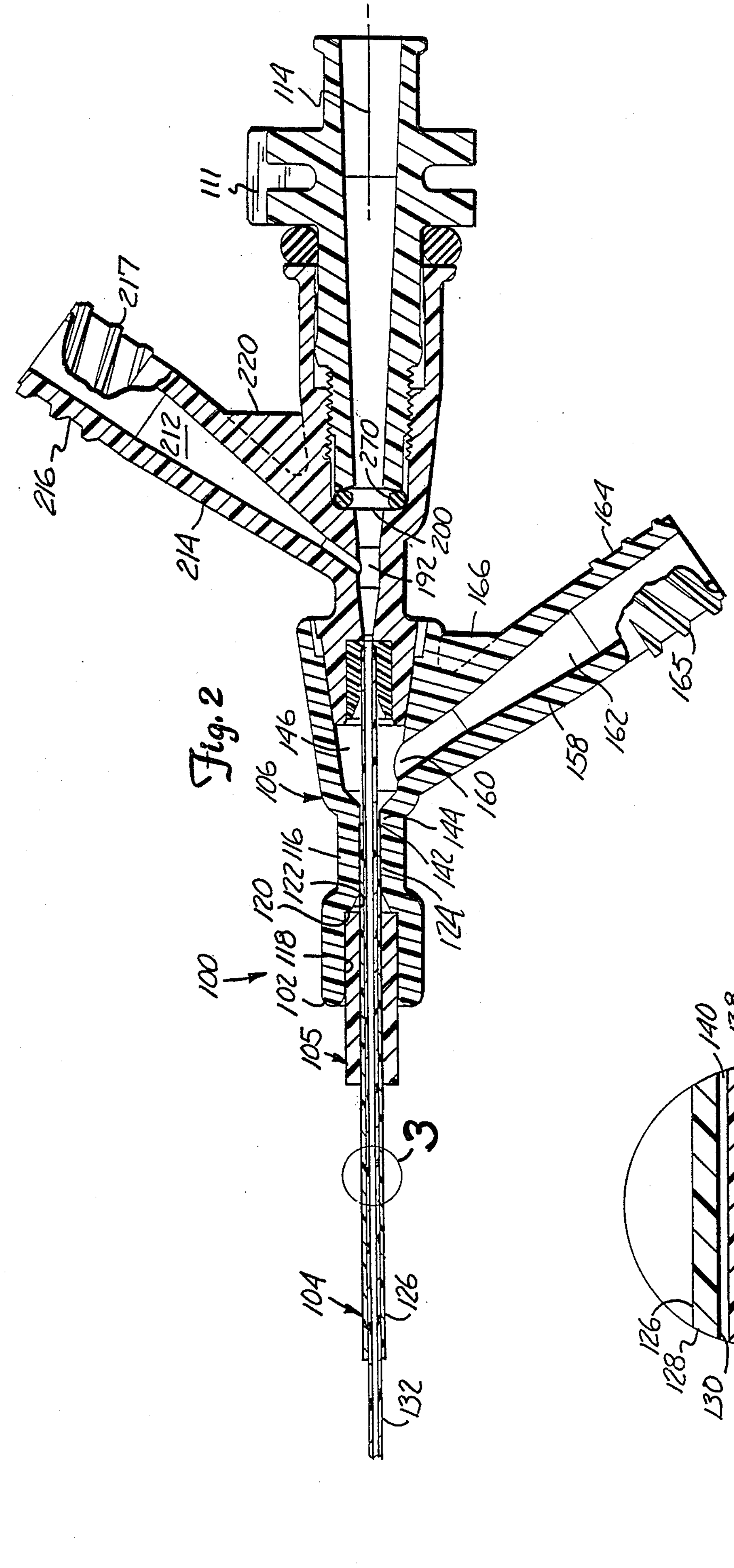
FIG. 2 is a horizontal sectional view of the preferred embodiment.
Figure 3:
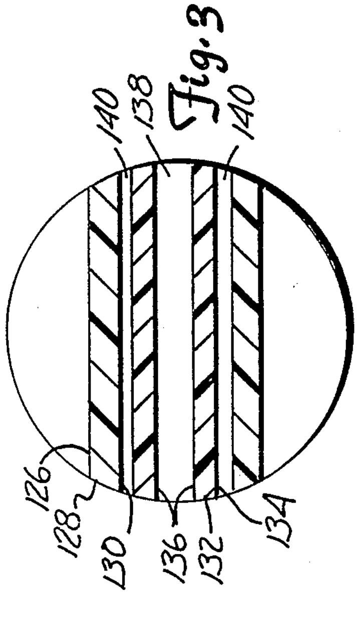
FIG. 3 is an enlarged fragmentary portion of the catheter sectional view of FIG. 2 at circle 3.

The detailed structure of the manifold 100 may be described, beginning generally at the distal end 102, and working toward the proximal end 103 as follows: The balloon manifold 106, as shown in FIG. 2, has a main body 116 which is generally symmetrical about the central axis 114. A distal bore 118 is sized to fit the strain relief sleeve 105. The strain relief sleeve 105 protects the catheter 104 from kinking adjacent the distal end 102 of the manifold 100. The distal bore 116 terminates in a step 120. The strain relief sleeve 105 abuts the step 120 within the balloon manifold 106. A tapered transition 122 from the step 120 is provided to an adjacent bore 124. The double lumen catheter 104, as shown in FIG. 3, has an outer tube 128. The outer tube 128 has an outer surface or wall 126 and an inner surface or wall 130. The adjacent bore 124 is sized to receive the outer surface 126 of the outer tube 128.

Contained within the inner surface 130 of the outer tube 128 is an inner tube 132 also having an outer surface or wall 134 and an inner surface or wall 136. The double lumen catheter 104 has a guide wire space or lumen 138 as defined by the inner surface 136 of the inner tube 132. An annular flow space or lumen 140 is defined by the inner surface 130 of the outer tube 128 and the outer surface 134 of the inner tube 132. The annular flow space 140 is in fluid connection with the expansion balloon (not shown).

Figure 4:
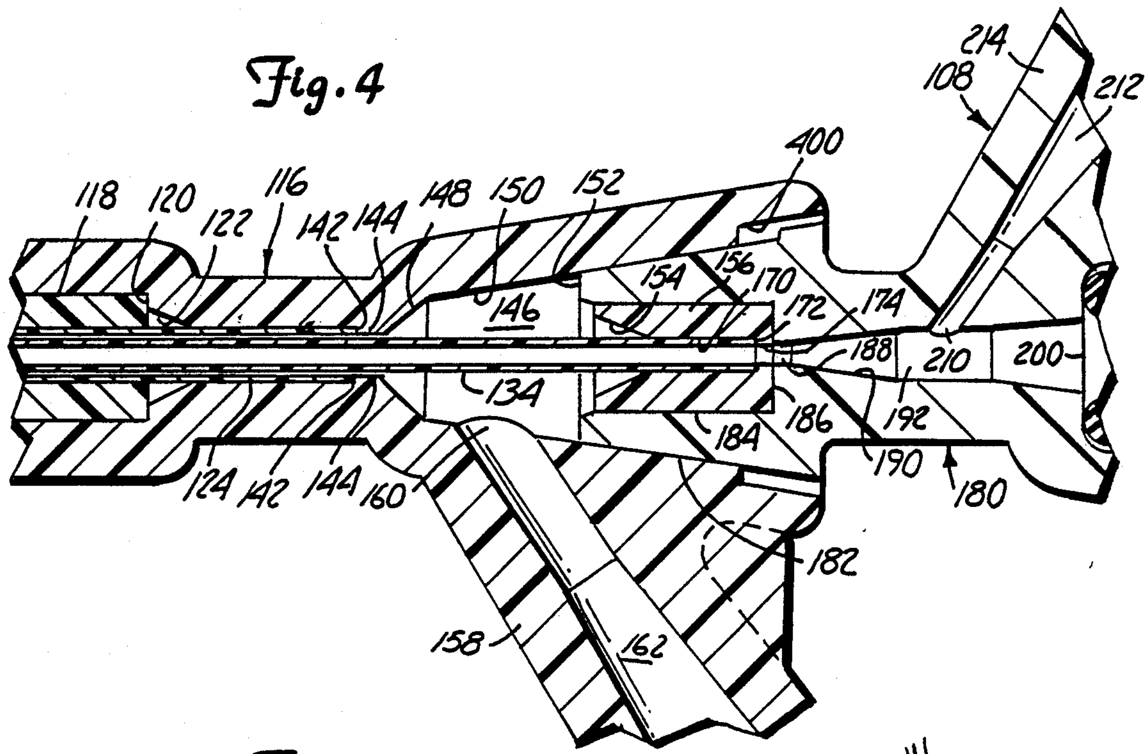
FIG. 4 is an enlarged fragmentary view of the chamber areas of the balloon and thru/dye manifolds of FIG. 2.

The adjacent bore 124, as shown in FIG. 4, also includes an inwardly directed stop 142 which is abutted by the outer tube 128. A connecting bore 144 leads from the step 142, to a chamber 146. The connecting bore 144 has a diameter approximately equal to the diameter of the inner surface 130 of the outer tube 128. The inner tube 132 continues past the stop 142 and the connecting bore 144 in such a manner that the annular flow space 140 is maintained in a relatively smooth and uninterrupted manner into the chamber 146.

The chamber 146, as shown in FIG. 4, is defined, in part, by a transition surface 148 which gradually increases in diameter from the connecting bore 144 to meet a female frustoconical surface 150 which also partially defines the chamber 146. The chamber 146 is further defined by a distal rim 152 of the thru/dye manifold 108 and a tapered portion 154 of an insert or sleeve 156. A side arm 158, as shown in FIG. 2, includes a port 160 opening onto the chamber 146, and a generally tubular passage 162 connecting the port 160 to a threaded connector 164. The tubular passage 162 has an angle of approximately 55° from the proximal direction of the central axis 114. The threaded connector 164 includes external threads 165 suitable for connecting to a balloon catheter inflation device. Inflation devices are well-known in this art. One particularly preferred inflation device is that disclosed by co-pending application Serial No. 165,600 filed Mar. 8, 1988.

A fillet 166 is proximally located between the main body 116 of the balloon manifold and the side arm 158 and serves to strengthen the side arm 158.

The insert 156, as shown in FIG. 4, has a generally cylindrical body symmetrically located with respect to the central axis 114. An intermediate bore 170 leads in a proximal direction from the tapered portion 154. The diameter of the intermediate bore 170 matches the diameter of the outer surface 134 of the inner tube 132. A step 172 at the proximal terminus of the bore 170 abuts the proximal end of the inner tube 132. A proximal orifice 174 has approximately the same diameter as the inner surface 136 of the inner tube 132.

The thru/dye manifold 108 also has a main body 180 which is generally symmetrical about the central axis 114. The thru/dye manifold 108 has a distally located male frustoconical surface 182 leading in a proximal direction from the distal rim 152. The male frustoconical surface 182 complements or mates with the female frustoconical surface 150 of the balloon manifold 106. A distal bore 184 also leads proximally from the distal rim 152. The bore terminates in a stop 186. The bore 184 has a diameter suitable for receiving the cylindrical body of the insert 156.

Additionally, the distance from the rim 152 to the stop 186 slightly exceeds the length of the insert 156. An orifice 188, identical in size and aligned with the orifice 174 of the insert 156, leads proximally from the stop 186 to an increasing taper or transitional surface 190 which defines the forward portion of a second chamber 192. The chamber 192 is further defined by a passageway leading to a guide wire entry port 200.

The second chamber 192 also includes a second port 210 connected to a tubular passage 212 within a side arm 214. The side arm terminates in a standard threaded connector 216 having male threads 217. The side arm 214 and associated port 210 provide an introduction site for a pressurized dye solution. When injected into the chamber 192, the dye solution flows through the guide wire lumen 138, into an annular space between the guide wire and the inner diameter 136 of the inner tube 132. The dye solution discharges into the artery undergoing the angioplasty procedure. The subsequent movement of the dye solution may be observed to determine in part the effectiveness of the procedure. Alternatively, the side arm 214 and port 210 may be utilized to measure blood pressure in the artery near the balloon catheter. The side arm 214 forms an angle of approximately 55° from the proximal extension of the central axis 114. A fillet 220 strengthens the side arm 214 with respect to the main body 180 of the thru/dye manifold 108.

The second port 210 lies on an opposite side of the axis from the first port 160 such that the side arms 158 and 214 lie in the same plane with the central axis 114, but lead off opposite sides of the manifold 100. The arrangement of the side arms 158 and 214 provide an adequate separation of the threaded connectors 164 and 216 such that a physician may conveniently access the manifold 100 to make connections to a suitable balloon catheter inflation device and a dye input or blood pressure measuring device.

Figure 5:
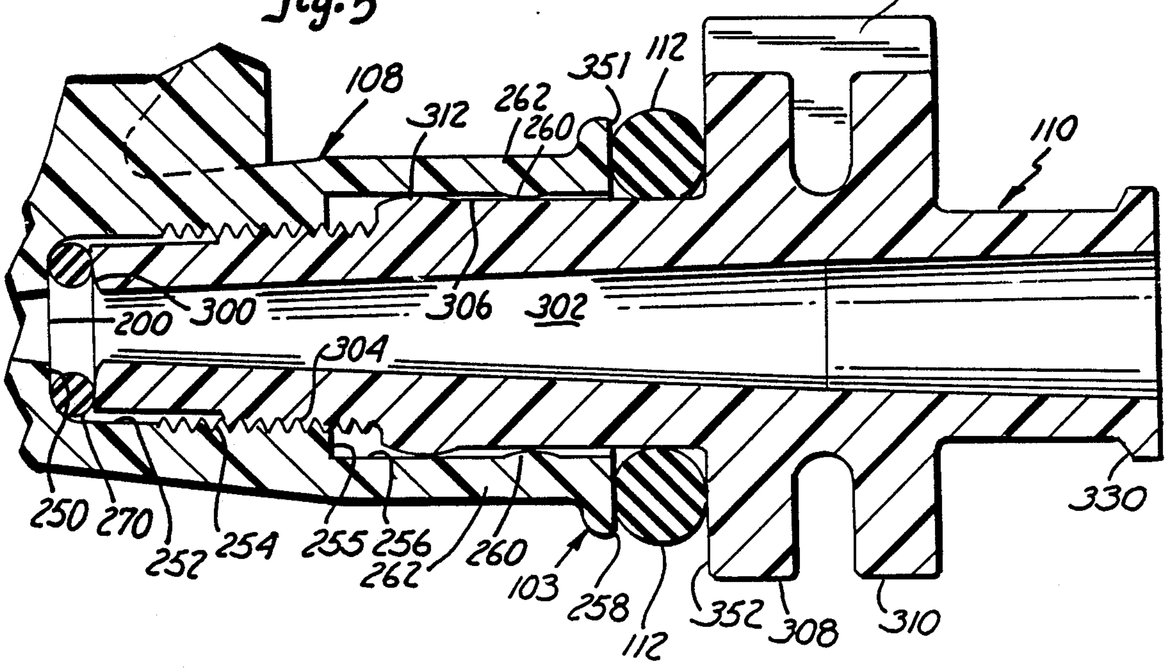
FIG. 5 is an enlarged fragmentary view of the guidewire entry port area of FIG. 2.

The guide wire entry port 200, as shown in FIG. 5, includes a sealing surface 250 which is perpendicular to and generally concentric about the central axis 114. A bore 252 leads proximally from the sealing surface 250 to a female threaded section 254. A proximal bore 256 is of greater diameter and leads proximally from a step 255 adjacent the female threaded section 254 to a radially extending shoulder or flange 258 at the proximal end 103 of the thru/dye manifold 108. The proximal bore 256 is formed within a cylindrical wall 262.

A pair of opposed rib projections 260 extend inward from the wall 262 and are located within the bore 256. The rib projections 260 lie within the same plane as the side arms 214 and 158. The ribs 260 intrude into the bore 256 narrowing the available diameter. The cylindrical wall 262, defining the bore 256 and carrying the ribs 260, and the flange 258 have a resilient nature. The wall 262 and flange 258 may be slightly resiliently deformed to alter the spacing between the ribs 260.

Abutting the sealing surface 250 and concentric about the central axis 114, is a wire sealing O-ring 270. The hemostatic valve nut 110 has a body with a concave distal rim or surface 300 leading to an axial through bore 302. The hemostatic valve nut 110 also includes a male threaded portion 304 which engages the female threaded portion 254 of the thru/dye manifold 108. Rotation of the hemostatic valve nut 110 advances the concave surface 300 deforming the wire sealing O-ring 270 to a progressively smaller diameter. The hemostatic valve nut 110 may be advanced to deform the O-ring 270 such that a seal is formed between the guide wire (not shown) and the sealing surface 250 to provide a seal at the proximal end of the chamber 192.

Effectively, the sealing diameter of the wire sealing O-ring 270 is adjustable by rotation of the hemostatic valve nut 110. The hemostatic valve nut 110 also includes a cylindrical surface 306 extending to a pair of radially extending disks or shoulders 308 and 310. The distal disk 308 and the proximal disk 310 have textured or knurled circumferential surfaces, as shown in FIG. 1, to facilitate gripping in order to rotate the hemostatic valve nut 110. By rotation of the valve nut 110, sealing or unsealing of the compression or wire sealing O-ring 270 against a guide wire may be achieved.

A single tab 111 extends from between the disks or shoulders 308 and 310. The tab 111 projects past the disks 308 and 310 and extends longitudinally over the textured surfaces. The tab 111 serves to provide an indication of the angular position of the hemostatic valve nut 110. Thus, the extent of sealing of the wire sealing O-ring 270 may be observed by a physician either visually or tactilely. During particularly crucial periods in the angioplasty procedure, the physician may tactilely recheck and/or reset the angular positioning of the hemostatic valve nut 110 without having to look at the manifold 100.

At the distal end of the cylindrical surface 306 is a segment 312 of increased diameter. The diameter of the segment 312 slightly exceeds the undeformed diameter between the ribs 260 intruding into the bore 256. In order for the increased diameter segment 312 to pass the ribs 260, the resilient wall 260 of the bore 256, as well as the flange 258, must be slightly deformed.

In use, the interaction between the segment 312 and the ribs 260 provides a snapping effect on the hemostatic valve nut 110 when withdrawn or inserted into the resilient bore 256. The resilient bore 256 and flange 258 may be alternatively described as a resilient proximal extension bore of the thru/dye manifold 108. In effect, the snapping action of the hemostatic valve nut 110 with respect to the thru/dye manifold 108 renders the hemostatic valve nut 110 captive to the manifold 100. In this way, inadvertent removal of the hemostatic valve nut 110 is avoided.

The captive or snapping relationship is particularly important since removal of the hemostatic valve nut 110 is a first step on the pathway to separation and loss of the hemostatic valve nut 110. Without the hemostatic valve nut 110, the entire catheter assembly is rendered useless. The loss, dropping or cross threading of the valve nut 110 is a particularly dangerous possibility during an angioplasty procedure since such an event consumes valuable time and is extremely distracting and frustrating to the operating physician.

However, the hemostatic valve nut 110 may be withdrawn from the manifold 100 when desired by exerting sufficient additional force to overcome the snapping action. The ability to overcome the snapping action when desired is another important feature of the invention.

Proximally located on the hemostatic valve nut 110 is a Luer fitting 330. The Luer fitting enables a physician to attach a Y-type adapter with an elastic diaphragm for inserting the guide wire. Such Y-type adapters with elastic diaphragms are well-known in the art. One such example is available from United States Catheter Corp. (USCI) (a division of C.R. Bard, Inc. of Billerica, Mass.) and is shown in the USCI catalog as Nos. 006055, 006056 or 006057. Thus, the proximal Luer fitting 330 on the hemostatic valve nut 110 offers the physician a choice between a compressive O-ring hemostatic valve seal and an elastic diaphragm seal.

In order to use the manifold 100 with a Y-type adapter with an elastic diaphragm, a physician removes the hemostatic valve nut 110 by rotating and unsnapping from the thru/dye manifold 108. A large O-ring 112 is then installed on the hemostatic valve nut 110 adjacent the distal radially extending plate 308. In a most preferred embodiment, the physician has available a sterile packaged hemostatic valve nut 110 with the larger O-ring 112 already in place. The larger O-ring 112 serves a number of useful purposes.

First, the face sealing O-ring 112 serves as a "spacer" by bearing against the proximal face 351 of the flange 258 and the distal face 352 of the distal radial extending disk 308. Effectively, the large O-ring 112 prevents the hemostatic valve nut 110 from interacting with the O-ring 270 located at the hemostatic valve and thereby prevents the wire sealing O-ring 270 from sealing against the guide wire.

Second, the face sealing O-ring 112 provides a sealing action between the hemostatic valve nut 110 and the thru/dye manifold 108 separate from the guide wire port 200, effectively extending the second chamber 192 to the Luer fitting 114.

Thirdly, the face sealing O-ring 112 provides a frictional lock between the hemostatic valve nut 110 and the thru/dye manifold 108 such that the hemostatic valve nut 110 is prevented from rotating. The frictional lock results from the frictional interaction of the face sealing O-ring 112 against the radially extending distal face 352 of the distal disk 308 and the proximal face 351 of the flange 258. Inadvertent rotation of the hemostatic valve nut 110 is a particularly likely possibility during the use of a Y-type adapter with an elastic diaphragm and the face sealing O-ring 112 prevents such rotation.

Another feature of the manifold 100 is the elegance of assembly during manufacture. During manufacture, the inner tube 132 of the catheter 104 is bonded within the intermediate bore 170 of the insert or sleeve 156. Insertion of the inner tube 132 is further facilitated by the female frustoconical surface 154 which serves to guide the tube 132 into the bore 170. The sleeve or insert 156 in turn is bonded within the distal bore 184 of the thru/-dye manifold 108. Insertion of the insert or sleeve 156 is facilitated by the ease of handling of the greater diameter of the insert 156 and the distal bore 184, as compared to the insertion of a relatively fine and flexible inner tube 132.

Figure 6:
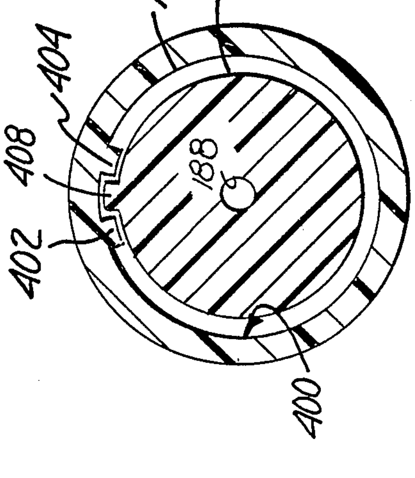
FIG. 6 is an enlarged fragmentary sectional view at line 6—6 of FIG. 1.

Additionally, the female frustoconical surface 150 of the balloon manifold 106 and the male frustoconical surface 182 of the thru/dye manifold are bonded together. An additional female frustoconical surface 400, as shown in FIG. 4, serves to neatly trap excess adhesive which may be squeezed from the joint as the balloon 106 and thru/dye 108 manifolds are assembled. Additionally, projecting inwardly on the second female frustoconical surface 400, as shown in FIG. 6, are a pair of spaced apart ribs 402 and 404 which encourage proper rotational alignment of the two manifolds. The thru/dye manifold 108 includes a projection 408 from the male frustoconical surface 182 which is centered between the two ribbed extensions 402 and 404 during assembly. The centering action facilitates assembly of the manifold 100 with the planar orientation of the side arms 158 and 214.

Another feature resulting from the assembly of the particular combination of component parts of this invention is that the path for the guide wire created by the assembly is relatively smooth (i.e. free of ledges or catches from either end of the manifold) such that a guide wire may be subsequently inserted from either end with relative ease. Effectively, the assembly results in a high degree of concentricity. The high degree of concentricity is particularly encouraged by the sleeve or insert 156, which eliminates the need for complex assembly protocols to align a relatively fine tube with a fine orifice.

The chambers 146 and 192 are relatively low in volume. Small chamber volumes are highly advantageous in priming balloon angioplasty catheters because such chambers have a reduced capacity to trap air bubbles. Additionally, such chambers more efficiently transmit a vacuum from an external pressure/vacuum device to the catheter lumen. A relatively efficient transmission of vacuum also speeds the balloon deflation cycle of the angioplasty procedure.

Additionally, when the chambers 146 and 192 within the manifold 100 are narrowed to relatively fine passages, the narrowing is always accomplished by a gradual tapering. An additional desirable result of the gradually narrowing arrangement of chambers 146 and 192 arrangement is the relatively low internal turbulence which tends to ease the flow of fluids through the manifold 100 and into the double lumen catheter 104. Efficient, non-turbulent flows are particularly important in the case of the radio contrast fluid employed to inflate distally located balloons (not shown) since inflation and deflation times are relatively critical in an angioplasty procedure. Failure to avoid extended inflation times in the balloon catheter results in a condition known as profound ischemia which is extremely painful to the patient.

The manifold materials are preferably molded polycarbonate, although alternative easily molded materials suitable for adhesive joining may be substituted. The preferred adhesive for a manifold of molded polycarbonate is polyurethane adhesive. Suitable alternative adhesives, compatible with the materials to be joined may be substituted. The O-rings 270 and 112 are preferably formed of silicone resilient type materials. Of course, alternative suitable O-ring materials may be substituted. An additional consideration in choosing materials is compatibility with sterilization protocols and compatibility with radiocontrast fluids or other fluids which may contact the manifold. In general, FDA regulations and approval should also be considered in choosing materials.

In summary, the manifold 100 of this invention is extremely versatile, allowing an operating physician a choice of either a compressive hemostatic valve seal to be employed or, alternatively, allowing the use of a Y-type adapter with an elastic diaphragm for inserting a guide wire. Additionally, the manifold 100 is exceptionally efficient to assemble, while maintaining a high degree of quality control in assembly. The manifold 100 has a high degree of concentricity, relatively small chamber volumes, and encourages relatively non-turbulent flows. Further, the captive aspect of the hemostatic valve nut avoids inadvertent separation of the valve nut from the manifold.

Although the present invention has been described with reference to preferred embodiments, workers skilled in the art will recognize that changes may be made in form and detail without departing from the spirit and scope of the invention.

What is claimed is:

1. An angioplasty device comprising:

an angioplasty balloon catheter having a first lumen extending therethrough in fluid connection with a distally located balloon and a second lumen extending therethrough capable of receiving a guide wire; and a manifold comprising:

a first chamber connecting the first lumen to a first port;

a second chamber connecting the second lumen to a second port and a guide wire entry port;

means for progressively and reversibly sealing the guide wire entry port about the guide wire; and means for coupling an elastic diaphragm guide wire feed through device to the means for reversibly sealing.

2. The device of claim 1 wherein the means for reversibly sealing comprise:

an object of resilient seal material and means to simultaneously force the object in sealing contact with the guide wire and the guide wire entry port.

3. The device of claim 2 wherein the object of resilient seal material is a wire engaging "O" ring and the means to simultaneously force is a hemostatic valve nut.

4. The device of claim 3 wherein the means for coupling is a Luer fitting on the hemostatic valve nut.

5. The device of claim 1 further comprising: means for locking the means for reversibly sealing in a desired sealing condition.

6. The device of claim 5 wherein the means for reversibly sealing includes an object of resilient sealing material and means for compressing the object and wherein the means for locking includes means for frictional locking between the manifold and the means for compressing.

7. The device of claim 6 further comprising:

a threaded portion; and wherein the means for compressing is a hemostatic valve nut engaging the threaded portion of the manifold.

8. The device of claim 7 further comprising:

a radially extending shoulder on the manifold;

a radially extending shoulder on the hemostatic valve nut; and wherein the means for frictional locking includes a frictional locking object engaging both radially extending shoulders.

9. The device of claim 8 wherein the frictional locking object is a face-sealing "O" ring interposed between the radially extending shoulders of the manifold and the hemostatic valve nut which frictionally locks the manifold and hemostatic valve nut.

10. The device of claim 5 wherein the desired sealing condition is the absence of a seal.

11. The device of claim 1 further comprising:

means for sealing the means for coupling to the second chamber.

12. The device of claim 11 further comprising:

a radially extending shoulder on the manifold;

a hemostatic valve nut;

a radially extending shoulder on the hemostatic valve nut; and wherein the means for coupling include a Luer fitting on the hemostatic valve nut and the means for sealing include a face-sealing "O" ring interposed between the radially extending shoulders of the manifold and hemostatic valve nut.

13. The device of claim 12 wherein the face-sealing "O" ring prevents a seal between the guide wire and the guide wire entry port.

14. The device of claim 1 wherein the means for reversibly sealing includes a hemostatic valve nut and wherein the manifold further comprises:

means to prevent inadvertent removal of the hemostatic valve nut.

15. The device of claim 14 wherein the means to prevent inadvertent removal includes a snap fit between the hemostatic valve nut and an extension of the second chamber.

16. An angioplasty device comprising:

an angioplasty balloon catheter having a first lumen extending therethrough in fluid connection with a distally located balloon and a second lumen extending therethrough capable of receiving a guide wire; and a manifold comprising:

a first chamber connecting the first lumen to a first port;

a second chamber connecting the second lumen to a second port and a guide wire entry port;

means for reversibly sealing the guide wire entry port about the guide wire; and means for preventing the inadvertent separation of the means for reversibly sealing from the manifold.

17. The device of claim 16 wherein the means for reversibly sealing includes a wire engaging "O" ring and a hemostatic valve nut for compressing the wire engaging "O" ring.

18. The device of claim 17 wherein the means for preventing the inadvertent separation includes a snapping arrangement between the hemostatic valve nut and the manifold.

19. The device of claim 18 wherein the snapping arrangement includes a resilient extension bore carrying the hemostatic valve nut and the bore includes at least one diameter narrowing intrusion, and the hemostatic valve nut includes a diameter increasing portion such that the resilient extension bore must be deformed for the diameter increasing portion of the hemostatic valve nut to pass the diameter narrowing intrusion of the resilient extension bore.

20. The device of claim 19 wherein the diameter narrowing intrusion is one of a pair of opposed rib projections.

* * * * *